United States Patent [19]

Misato et al.

[11] 3,947,589
[45] Mar. 30, 1976

[54] FUNGICIDAL METHODS EMPLOYING AMINO ACID DERIVATIVES

[75] Inventors: Tomomasa Misato, Tokyo; Keng Tang Huang, Wako; Yasuo Homma, Fukuoka; Seizo Kanao, Tokyo; Takeshi Toyoda, Sagamihara; Tadashi Suyama; Toshiro Shida, both of Kawasaki, all of Japan

[73] Assignees: Rikagaku Kenkyusho, Saitama; Ajinomoto Co. Ltd., Tokyo, both of Japan

[22] Filed: May 9, 1974

[21] Appl. No.: 468,266

Related U.S. Application Data

[63] Continuation of Ser. No. 219,554, Jan. 20, 1972, abandoned.

[30] Foreign Application Priority Data

Jan. 23, 1971   Japan.................................. 46-1833
June 26, 1971   Japan................................ 46-46024

[52] U.S. Cl.............................. 424/319; 260/534 R
[51] Int. Cl.².............................................. A01N 9/20
[58] Field of Search........................... 424/312, 319

[56] References Cited
UNITED STATES PATENTS

| | | | |
|---|---|---|---|
| 2,965,534 | 12/1960 | Darlington.......................... | 424/312 |
| 3,758,525 | 9/1973 | Yoshida et al...................... | 424/319 |

OTHER PUBLICATIONS
Chemical Abstracts, Vol. 60, 1964, p. 15,517(b).

*Primary Examiner*—V. D. Turner
*Attorney, Agent, or Firm*—Sherman & Shalloway

[57] ABSTRACT

N-Higher aliphatic amino acids, lowe-alkyl esters thereof and their salts are useful for controlling numerous plant diseases. They exhibit excellent protective effect rather than curative effect and have no phytotoxicity, extremely low mammalian toxicity and cause no risk of pollution toward soils.

7 Claims, No Drawings

FUNGICIDAL METHODS EMPLOYING AMINO ACID DERIVATIVES

This is a continuation of application Ser. No. 219,554, filed Jan. 20, 1972, now abandoned.

The present invention relates to an agricultural and horticultural fungicidal agent and to a method for the use thereof, and more particularly the present invention relates to fungicidal compositions for agricultural and horticultural use in which N-higher aliphatic acyl amino acids having an aliphatic acyl group of 8 – 22 carbon atoms, lower alkyl esters thereof and their salts are the active ingredients. The term "fungicidal composition or agent", as used in the present specification and claims, is meant to also include a bactericidal composition or agent.

Compounds of heavy metals such as copper, mercury and arsenic, as well as organophosphorus and organic chlorine compounds have been practically used for the control of plant diseases, but each of these fungicides cannot be necessarily said to be satisfactory one, because of its pollution toward soils, its strong medicinal harm on plants, its residual toxicity in food crops, its high mammalian toxicity or its irritation to skin and eyes of human.

As the result of having ardently studied compounds which do not possess any of the above faults as recognized in the fungicides previously used and which exhibit preventive effect against the fungal plant diseases, it has now been found that N-higher aliphatic acyl amino acids, lower alkyl esters thereof and their salts exhibit excellent preventive effect against numerous plant diseases such as rice blast and rice leaf blight which are the main diseases of rice plants citrus melanose, cucumber anthracnose, cucumber phytophthora rot, cucumber powdery mildew, cucumber downy mildew, tomato leaf mold, tomato late blight, tomato leaf spot and others, and that they have no phytotoxicity and have extremely low mammalian toxicity and cause no risk of pollution toward soils.

The N-Higher aliphatic acyl amino acids, lower alkyl esters thereof or their salts which may be employed as the active ingredients of the fungicidal compositions of the present invention are amino acid derivatives having a higher aliphatic acyl group introduced into the amino group of various amino acids or lower alkyl esters thereof. The higher aliphatic acyl radical may be any one derived from saturated or unsaturated fatty acids having 8 to 22 carbon atoms, preferably 12 to 18 carbon atoms, for example, an acyl radical derived from a single fatty acid (such as decanoic acid, lauric acid, palmitic acid, stearic acid, oleic acid or linolenic acid), an acyl radical derived from a naturally originating mixed fatty acid (such as coconut oil fatty acid) or an acyl radical derived from the synthetic fatty acid (inclusive of a branched chain fatty acid).

The amino acid components are acidic amino acids such as glutamic acid, aspartic acid, a-aminopemalic acid, $\alpha$-aminopimeric acid, diaminodicarboxylic acids such as $\alpha,\alpha'$-diaminocitric acid, $\alpha,\alpha'$-diaminoglutaric acid and $\alpha,\alpha'$-diaminoadipic acid; neutral amino acids such as glycine, phenylglycine, alanine, $\alpha$-aminobutyric acid, valine, norvaline, leucine, isoleucine, norleucine, phenylalanine, p-nitrophenylalanine, tryptophane and proline; basic amino acids such as lysine, ornithine, arginine, histidine, citrulline, and isolysine. Other example of the neutral, acidic, and basic amino acids are sulfur-containing amino acids such as methionine, cysteine, cystine, homocystine, penicillamine, $\beta$-thiolleucine and ethionine; hydroxyamino acids such as threonine, serine, tyrosine, nitrotyrosine, $\beta$-hydroxyleucine, homoserine and oxyproline; N-methyl or N-ethyl derivatives of those $\alpha$-amino acids; $\omega$-lower alkyl esters of acidic amino acids such as glutamic and aspartic acids; lower alkyl esters of basic amino acids such as lysine, ornithine, arginine and citrulline; O-acyl or O-methyl derivatives of hydroxyamino acids; $N^{\omega}$,$N^{\omega}$-di-lower alkyl or $N^{\omega}$-acyl derivatives of basic amino acids such as lysine and ornithine. In addition to these $\alpha$-amino acids, $\beta$-amino acids such as $\beta$-alanine and $\beta$-aminoisobutyric acid; amino acids such as $\gamma$-aminovaleric acid and $\omega$-aminocaproic acid, and N-methyl, N-ethyl derivatives of these amino acids may be also employed. These amino acids or their derivatives may be optically active L- and O- forms or racemic form.

Among the N-higher aliphatic acyl amino acid lower alkyl esters, especially $N^{\alpha}$-higher aliphatic acyl basic amino acid lower alkyl esters are preferable, because of their excellent preventive effect against plant diseases. In this case, suitable lower alkyl esters are those containing 1 to 4 carbon atoms such as methyl, ethyl, propyl and butyl esters.

As the salts of N-higher aliphatic acyl amino acids, alkali metal salts such as lithium, sodium and potassium salts, ammonium salt, and salts with organic bases such as methylamine, triethylamine, diethylamine and ethanolamine may be employed. Also $N^{\alpha}$-higher aliphatic acyl lower alkyl esters may be employed in the form of their acid addition salts, especially their non-phytotoxic salt. Examples of such acid addition salts are salts with inorganic acids such as hydrochloric acid and sulfuric acid; and salts with organic acids such as optically active or inactive pyroglutamic acid, optically active or inactive acidic amino acid (e.g. glutamic or aspartic acid), lactic acid, citric acid, acetic acid and the like.

N-Higher aliphatic acyl amino acids may be easily obtained by the well-known method in which an amino acid is reacted with a higher aliphatic acyl halide having 8 – 22 carbon atoms in the presence of a suitable inorganic or organic base such as sodium hydroxide, potassium hydroxide or triethylamine. $N^{\alpha}$-higher aliphatic acyl basic amino acid lower alkyl esters may also be easily obtained at low cost by the known method, but they are usually obtained in the form of their acid addition salts from the point of view of crystalline nature. For example, $N^{\alpha}$-higher aliphatic acyl derivative of a basic amino acid lower alkyl ester salt selected from the group consisting of arginine lower alkyl ester salt, histidine lower alkyl ester salt and citrulline lower alkyl ester salt may be obtained from the corresponding basic amino acid lower alkyl ester salt by the method in which the basic amino acid lower alkyl ester salt is dissolved in an organic solvent such as chloroform or benzene and acylated by reacting with a higher fatty acid halide having 8 – 22 carbon atoms in the presence of an organic amine such as triethylamine and thereafter the resulting product is contacted with an inorganic or organic acid. Also, for the preparation of $N^{\alpha}$ -higher aliphatic acyl derivative of basic amino acid lower alkyl esters selected from the group consisting of ornithine lower alkyl ester salt and lysine lower alkyl ester salt, $N^{\omega}$-substituted basic amino acid lower alkyl ester, amino group at the $\omega$-position being substituted with a suitable protective radical such as carbobenzoxy radical, is reacted with a higher fatty acid halide according to the similar manner as in the above to produce the corresponding $N^\omega$-substituted-$N^\alpha$-higher aliphatic acyl derivative, from which the protective group is liberated and thereafter the resulting product is contacted with an inorganic or organic acid.

The outstanding feature of the active ingredients of the fungidical compositions of the present invention is that although they do not show an appreciable fungicidal or bactericidal activity against plant disease fungi or bacteria in vitro test, they exert noticeable preventive effect for the first time when applied to plants in vivo test and they have not phytotoxic effect on the plants and show an appreciable plant growth promoting action.

The active ingredients of the present invention is especially useful in controlling the following susceptible fungi (and bacteria) which attack food crops: *Pirocularia oryzae*, the organism which causes rice blast; *Xantomonas oryzae*, the organism which causes rice leaf blight; citrus melanose; *Colletotrichum lagenarium*, the organism which causes cucumber anthracnose; *Phytophthora parasitica*, the organism which causes cucumber phytophthora rot; *Sphaerotheca fuliginea*, the organism which causes cucumber powdery mildew; *Pseudoperonospore cubensis*, the organism which causes the cucumber downy mildew; *Cladosporium fulvum*, the organism which causes tomato leaf mold; *Phytophthora fulvum*, the organism which causes tomato leaf mold; *Phytophthora fulvum*, the organism which causes tomatoe late blight; *Stemphylium lycopersici*, the organism which causes tomato leaf spot and others.

The active ingredients of the fungicides in the present invention may be directly applied to the susceptible plant surface or they may be applied thereto in any formulation such as granules, dusts, emulsifiable concentrates, wettable powders, pastes, oil agents, aerosols, fogs or fumigants with suitable solid carriers, liquid carriers, emulsifying and dispersing agents and so on, in a manner similar to the formulations well-known in the art. Examples of these carriers include clay, kaoline, bentonite, acidic terra abla, diatoraceous earth, calcium carbonate, nitrocellulose, starch, acacia, carbon dioxide gas, freon and the like. Also, auxiliary agents, which are usually employed in formulations, e.g. surface active agents which serve as spreads, dispersing and emulsifying agents may be adequately compounded. Examples of such surface active agents are soap, higher alcohol sulfate, alkyl sulfonate, alkylaryl sulfonate, quaternary ammonium salt, polyalkylene oxide and the like. The preferred concentration of the active ingredient in the fungicidal composition is about 5 – 95% by weight for use as emulsifiable concentrates or wettable powders, while the preferred concentration about 0.1 – 50% by weight for use as dusts or oil agents. However, these concentrations may be adequately varied depending on the purpose of use.

The amount of the fungicidal composition to be applied may vary according to such factors as the formulation of the composition, the type of the active ingredient, or the concentration of the active ingredient in the composition. Usually, it is about 10 g/10 ares to 2000 g/10 ares, preferably 50 g/10 ares to 1000 g/10 ares, as the active ingredient. If desired, greater amounts can be applied.

The active ingredients of this invention may also be employed in admixture with herbicides, insecticides, other fungicides, soil conditioners and fertilizers such as urea, ammonium sulfate, ammonium phosphates, potassium salts and so on.

The results of an acute oral toxicity test of the active ingredient used in the present invention is that its $LD_{50}$ is about 6 g/kg in the case of N-lauroyl-L-valine. This is an extremely low toxicity.

One example of a test to determine pollution toward soils will be shown below.

In order to estimate rapid degradation of N-lauroyl-L-value by microorganisms, utilization of N-lauroyl-L-valine as sources of carbon and nitrogen by aerobic bacteria in the scale of a test tube was examined.

Microorganisms: Nine kinds of aerobic bacteria were used.

Culture medium: 0.1% $KH_2PO_4$. 0.04% $MgSO_4$. $7A_2O$. 3% $CaCO_3$. 0.05% Yeast extract (Difco) 1.0% Sodium N-Lauroyl-L-valinate pH 7.0. Total volume is 10 ml in each test tube (60 ml. vol.).

Culture method: A loopfull of cells grown on a bouillon agar slant for 24 hrs. at 30°C was inoculated into a test tube. Shaking culture was performed for 48 hrs. at 28°C.

Results are shown in Table A.

Table A

| Microorganisms | AJ. No. | Other No. | | State of Growth |
|---|---|---|---|---|
| Pseudomonas aeruginosa | AJ 2116 | ATCC | 10145 | ++++ |
| Ps. ovalis | AJ 2011 | IAM | 1002 | +++ |
| Ps. desmoyltica | AJ 2003 | IAM | 1089 | ++ |
| Achromobacter guttatus | AJ 2410 | | | ++++ |
| Flavobacterium citreum | AJ 2452 | IAM | 1158 | + |
| Serratia marcescens | AJ 2682 | IAM | 1021 | ++ |
| Micrococcus flavus | AJ 1021 | ATCC | 400 | + |
| Bacillus cereus | AJ 1264 | IAM | 1029 | + |
| Corynebacterium equi | AJ 1376 | | | + |

The state of growth was measured by eye-measurement.

The following examples illustrate the production of various formulations for application of the fungicidal composition according to this invention. Parts are given therein as parts by weight.

EXAMPLE 1

Twenty parts of N-lauroylglycine, 2 parts of white carbon, 2 parts of sodium lignin sulfonate, 4 parts of polyoxyethylene alkyl ether and 72 parts of clay were mixed together and milled to obtain 100 parts of wettable powder.

EXAMPLE 2

Two parts of N-cinnamoyl-L-phenylalanine and 98 parts of talcum were mixed to obtain 100 parts of dust.

EXAMPLE 3

Twenty parts of N-stearoyl-DL-alanine, 10 parts of a mixture of a mixture of polyoxyethylene alkyl allyl ether and sodium alkylaryl sulfonate, 20 parts of methanol and 50 parts of water were mixed until a suspension was formed. As a result, 100 parts of an emulsifiable concentrate were obtained.

EXAMPLE 4

Ten parts of N-lauroyl-DL-p-nitrophenylalanine, 15 parts of starch, 72 parts of bentonite and 3 parts of sodium lauryl alcohol sulfate were mixed together and milled to obtain 100 parts of granules.

The evaluation of the effectiveness of the fungicidal compositions of this invention against numerous plant disease fungi was accomplished by the following experimental examples.

Experimental Example 1: inhibitory test against rice blast disease (in pot test)

Rice stubbles (variety "Jukkoku") were planted in synthetic resin pots of 6 cm in diameter, ten rice stubbles being planted per pot and were grown in the greenhouse. Various wettable powders prepared according to Example 1 were diluted with water to 500 ppm as the final concentration of test compound and each of the dilute aqueous solutions was applied to the rice plant seedlings of the 4-leaf stage at a rate of 50 ml per pot using a spray-gum, and allowed to dry.

Spores of rice imochi blast (*Piricularia cryzae*) which had been cultivated in a chaff culture medium containing yeast extract, soluble starch, saccharose and chaff were suspended in water; and sprayed inoculation on the rice plant seedlings uniformly. The rice plant seedlings treated in the above manner were placed in an inoculation box at 28°C. and relative humidity of above 95% to be infected with Piricularia oryzae. Two days after infection, the number of disease lesions per leaf were counted and the preventive value was calculated according to the following equation:

$$\text{Preventive value (\%)} = \left(1 - \frac{\text{number of disease lesions of treated leaf}}{\text{number of disease lesions of untreated leaf}}\right) \times 100$$

The results obtained were as shown in Table 1.

Table 1

| No. of test compound | Average number of disease lesions per leaf | Preventive value (%) | Phytotoxicity |
| --- | --- | --- | --- |
| 1 | 1.7 | 95 | — |
| 2 | 6.6 | 80 | — |
| 3 | 8.9 | 73 | — |
| 4 | 7.3 | 78 | — |
| 5 | 11.0 | 67 | — |
| 6 | 6.6 | 80 | — |
| 7 | 5.9 | 82 | — |
| 8 | 11.0 | 67 | — |
| 9 | 9.9 | 70 | — |
| 10 | 11.6 | 65 | — |
| 11 | 7.6 | 77 | — |
| 12 | 11.6 | 65 | — |
| 13 | 8.9 | 73 | — |
| 14 | 5.6 | 83 | — |
| 15 | 7.4 | 88 | — |
| 16 | 11.0 | 67 | — |
| 17 | 5.9 | 82 | — |
| 18 | 10.7 | 68 | — |
| 19 | 7.3 | 78 | — |
| 20 | 9.9 | 70 | — |
| "Kitazin-P" | 6.9 | 79 | — |
| Untreated plant | 33.0 | 0 | |

(Note)
Test compounds
No. 1 : N-lauroylglycine
No. 2 : N-lauroyl-L-valine
No. 3 : N-lauroyl-DL-P-nitrophenylalanine
No. 4 : N-stearoyl-L-phenylalanine
No. 5 : N-oleoylglycine
No. 6 : sodium N-stearoylglycinate
No. 7 : N-stearoyl-DL-alanine
No. 8 : sodium N-lauroylphenylalaninate
No. 9 : N-myristoylglycine
No. 10 : sodium N-lauroyl-L-aspartate
No. 11 : N-lauroyl-L-threonine
No. 12 : N-caprinoyl-L-phenylalanine
No. 13 : N-lauroyl-L-leucine
No. 14 : N-undecylenoyl-L-leucine
No. 15 : N-lauroylsarcosine
No. 16 : N-caprinoyl-DL-methionine
No. 17 : N-cocoyl*-DL-valine
  *cocoyl: residue of coconut oil fatty acid Table 1-continued

| No. of test compound | Average number of disease lesions per leaf | Preventive value (%) | Phytotoxicity |
| --- | --- | --- | --- |

No. 18 : N-oleoyl-DL-isoleucine
No. 19 : N-lauroyl-L-valine ethyl ester
No. 20 : sodium N-myristoyl-L-glutamate
Control fungicide "Kitazin-P" (trade name, product of Kumiai Chemical Industrial Co., Ltd. emulsifiable concentrate containing S-benzyl O,O'-diisopropyl phosphorothiolate) was sprayed at 500 ppm. -: no phytotoxicity was observed.

Similar inhibitory tests against rice blast were conducted with various wettable powders containing $N^\alpha$ - higher aliphatic acyl basic amino acid lower alkyl esters instead of the N-higher aliphatic acid as an active ingredient. The results obtained are summarized in Table 2.

Table 2

| No. of test compound | Average number of disease lesions per leaf | Preventive value (%) | Phytotoxicity |
| --- | --- | --- | --- |
| 21 | 8.5 | 75 | — |
| 22 | 2.4 | 93 | — |
| 23 | 6.2 | 82 | — |
| 24 | 7.3 | 78 | — |
| 25 | 5.1 | 85 | — |
| 26 | 6.2 | 82 | — |
| 27 | 6.8 | 80 | — |
| 28 | 7.3 | 78 | — |
| "Kitazin-P" | 6.5 | 81 | — |
| Untreated plant | 34.2 | 0 | |

(Note)
Test compounds
No. 21 : $N^\alpha$-myristoyl-L-arginine ethyl ester.DL-pyroglutamate
No. 22 : $N^\alpha$-cocoyl-L-arginine ethyl ester.DL-pyroglutamate
No. 23 : $N^\alpha$-myristoyl-L-lysine methyl ester hydrochloride
No. 24 : $N^\alpha$-lauroyl-L-ornithine methyl ester hydrochloride
No. 25 : $N^\alpha$-myristoyl-L-histidine methyl ester hydrochloride
No. 26 : $N^\alpha$-lauroyl-L-citrulline methyl ester.DL-pyroglutamate
No. 27 : $N^\alpha$-lauroyl-L-arginine ethyl ester.DL-pyroglutamate
No. 28 : $N^\alpha$-stearoyl-L-arginine ethyl ester.DL-pyroglutamate Experimental example 2: inhibitory test against rice leaf blight On the rice plant needlings of the 4 – 5 - leaf stage grown in the greenhouse similarly to Experimental example 1, each of the dilute aqueous solutions (concentration of test compound: 500 ppm) of various wettable powders prepared according to Example 1 was sprayed at a rate of 50 mL per pot and then allowed to dry.

Cells of bacterial leaf blight (*Xantomonas oryzae*) cultivated in a bacterial leaf blight culture medium at 27°C for 3 days were suspended in water and inoculated with a needle to the highest and second highest leaves of the rice plant. In two to three weeks after inoculation, these leaves were infected with Xantomonas oryzae and the length of disease lesion per stalk was measured for the evaluation of effectiveness. The preventive value was calculated according to the following equation:

$$\text{Preventive Valve (\%)} = \left(1 - \frac{\text{length of disease lesion of treated leaf}}{\text{length of disease lesion of untreated leaf}}\right) \times 100$$

The obtained results were as shown in Table 3.

Table 3

| No. of test compound | length of disease lesion per stalk (mm) | Preventive value (%) | Phytotoxicity |
| --- | --- | --- | --- |
| 2 | 30.2 | 59 | — |
| 3 | 37.5 | 50 | — |
| 6 | 29.3 | 61 | — |
| 7 | 27.0 | 64 | — |
| 8 | 35.3 | 53 | — |
| 9 | 32.3 | 57 | — |
| 10 | 34.5 | 54 | — |
| 11 | 29.3 | 61 | — |
| 15 | 25.5 | 66 | — |
| 16 | 31.5 | 58 | — |
| 18 | 30.0 | 60 | — |
| "Kumiai Phenazine" | 15.2 | 80 | — |
| "Mikasa Sunkel" | 26.2 | 60 | — |
| Untreated plant | 75 | 0 | |

(Note)
Nos. of test compounds used are the same as those of test compounds in table 1.
"Kumiai Phenazine" (trade name, product of Kumiai Chemical Industrial Co., Ltd., wettable powder containing phenazine 5-oxide) was sprayed at 62 ppm.
"Mikasa Sunkel" (trade name, product of Mikasa Chemical Industrial Co., Ltd., wettable powder containing nickel dimethyldithiocarbamate) was sprayed at 1500 ppm.

Experimental example 3: inhibitory test against Citrus melanose
a. Test plant: shoots of about 3 years grown seedlings of citrus "Onshu" (2 – 4 trees planted in about 20 cm claypot)
b. Solution used for test
Each of various wettable powders prepared according to Example 1 was diluted with water to 500 ppm as the final concentration of test compound and then sprayed uniformly on the test plants at a rate of 40 ml per two claypots.
As control fungicide, "Daisen" [trade (trade name, product of Nihon-Nohyaku Co., Ltd., wettable powder containing zinc ethylene bis (dithiocarbamate)] was sprayed at 1000 ppm.
c. Inoculum and the method of inoculation
In order to prepare suspension of pycnospores, distilled and sterilized water was poured on the culture twigs with citrus melanose in a test tube. The suspension containing about 200 of pycnospores was prepared under the observation of microscope of 150 magnification and then sprayed inoculation on the test plants treated as above. After inoculation, the test plants were placed in the inoculation box at 27°C and relative humidity of above 95% for about 3 days. Then, they were transferred into the greenhouse.
d. The method of inspection
About 2 – 3 weeks after inoculation, the entire leaves of shoots was inspected for the development of disease and the state of infection was evaluated on a scale of 0 to 3 as follows:
0 : no disease
1 : 1 — 50 of disease spots
2 : 51 — 150 of disease spots
3 : above 151 of disease spots
The extent of infection and the preventive value were calculated according to the following equations (I) and (II), respectively.

(I) Extent of infection $= \dfrac{1 \times n_1 + 2 \times n_2 + 3 \times n_3}{3 \times N} \times 100$ wherein $n_1$, $n_2$ and $n_3$ are number of leaves inspected to be the states of infection 1, 2 and 3, respectively and N is the total number of leaves.

(II) Preventive value (%) $= \left(1 - \dfrac{\text{extent of infection of treated leaves}}{\text{extent of infection of untreated leaves}}\right) \times 100$ e. The results obtained were as shown in Tables 4 and 5.

Table 4

| | (N-acyl amino acid) | | |
| --- | --- | --- | --- |
| No. of test compound | Extent infection (%) | Preventive value (%) | Phytotoxicity |
| 1 | 15 | 72 | — |
| 3 | 26 | 50 | — |
| 4 | 21 | 60 | — |
| 6 | 17 | 68 | — |
| 8 | 22 | 59 | — |
| 10 | 14 | 74 | — |
| 14 | 19 | 65 | — |
| 16 | 24 | 54 | — |
| 18 | 26 | 50 | — |
| "Daisen" | 20 | 62 | — |
| Untreated plant | 53 | 0 | |

(Note)
Nos. of test compounds used are the same as those of test compounds in Table I Table 5

| | ($N^{\alpha}$-acyl basic amino acid ester) | | |
| --- | --- | --- | --- |
| No. of test compound | Extent of infection (%) | Preventive value (%) | Phytotoxicity |
| 21 | 15 | 73 | — |
| 22 | 17 | 70 | — |
| 23 | 21 | 64 | — |
| 24 | 18 | 68 | — |
| 27 | 14 | 75 | — |
| 28 | 15 | 73 | — |
| "Daisen" | 16 | 71 | — |

Table 5-continued (Nᵅ-acyl basic amino acid ester)

| No. of test compound | Extent of infection (%) | Preventive value (%) | Phytotoxicity |
|---|---|---|---|
| Untreated plant | 57 | 0 | |

(Note)
Nos. of test compounds used are the same as those of test compounds in Table 2.

Experimental example 4: inhibitory test against cucumber downy mildew

Cucumber seeds (variety "Shinhikari No. A") were planted in seed-beds at the biginning of October, three cucumber seeds being planted per seed-bed, and they were grown in a greenhouse made of vinyl resin. This experiment was performed as three-repeated cultivation.

Each of various wettable powders prepared according to Example 1 was diluted with water to 500 ppm as the final concentration of test compound and sprayed on the cucumber seedlings using a shouldering-sprayer four times in total on the 30th of April, the 6th, 12th and 19th of May so as to wet both sides of the leaves thoroughly with the liquid dispersion each time. The test plants treated thus were left to spontaneous infection. On the 23rd of May, the state of infection was inspected with respect to both sides of ten leaves ranging from the 11th to 20th leaf, and the preventive value was calculated according to the following equation:

Preventive value (%) = $\left(1 - \frac{\text{number of leaves infected in treated plant}}{\text{number of leaves infected in untreated plant}}\right) \times 100$ The results obtained were as shown in Tables 6 and 7.

Table 6

| No. of test compound | (N-acyl amino acid) | | | | |
|---|---|---|---|---|---|
| | Number of leaves infected (outside) | Preventive value (%) | Number of leaves infected (inside) | Preventive value (%) | Phytotoxicity |
| 1 | 4 | 67 | 6 | 73 | — |
| 3 | 6 | 50 | 9 | 59 | — |
| 4 | 7 | 42 | 10 | 47 | — |
| 7 | 5 | 58 | 8 | 64 | — |
| 8 | 3 | 75 | 7 | 68 | — |
| 9 | 7 | 42 | 9 | 59 | — |
| 12 | 4 | 67 | 6 | 73 | — |
| 13 | 7 | 42 | 9 | 59 | — |
| 18 | 5 | 58 | 7 | 68 | — |
| "Daconil" | 6 | 50 | 12 | 45 | — |
| Untreated plant | 12 | 0 | 22 | 0 | |

(Note)
Nos. of test compounds used are the same as those of test compounds in Table 1.

"Daconil"(trade name, product of Kumiai Chemical Industrial Co., Ltd., wettable powder containing tetrachloroisophthalonitrile) was sprayed at 1250 ppm.

Table 7

| No. of test compound | (Nᵅ-acyl basic amino acid ester) | | | | |
|---|---|---|---|---|---|
| | Number of leaves infected (outside) | Preventive value (%) | Number of leaves infected (inside) | Preventive value (%) | Phytotoxicity |
| 21 | 5 | 55 | 8 | 47 | — |
| 22 | 7 | 45 | 9 | 40 | — |
| 23 | 7 | 45 | 8 | 47 | — |
| 24 | 6 | 52 | 8 | 47 | — |
| 27 | 6 | 52 | 9 | 40 | — |
| "Daconil" | 5 | 55 | 7 | 53 | — |
| Untreated plant | 13 | 0 | 15 | 0 | |

(Note)
Nos. of test compounds used are the same as those of test compounds in Table 2.

It will be understood from the results of inhibitory and phytotoxic tests that the active ingredients of the present invention exhibit satisfactory effect in controlling numerous plant diseases and have no phytotoxicity.

What we claim is:

1. A method of protecting plants from attack by plant disease fungi or bacteria which comprises applying onto a fungus-susceptible plant a fungicidal amount of a compound selected from the group consisting of an N-acyl derivative of a neutral amino acid wherein said acyl moiety is selected from the group consisting of decanoic acid, lauric acid, palmitic acid, stearic acid, oleic acid, linolenic acid, coconut oil fatty acid, myristic acid, capric acid and undecylenic acid and said neutral amino acid is selected from the group consisting of glycine, phenylglycine, alanine, α-aminobutyric acid, valine, norvaline, leucine, isoleucine, norleucine, phenylalanine, p-nitrophenylalanine, tryptophane, proline, methionine, threonine and sarcosine or the lithium, sodium, potassium or ammonium salts of said N-acyl derivative of a neutral amino acid.

2. The method of claim 1 wherein said N-acyl derivative of an amino acid is N-lauroylglycine.

3. The method of claim 1 wherein said N-acyl derivative of an amino acid is N-lauroylsarcosine.

4. The method of claim 1 wherein said N-acyl derivative of an amino acid is N-stearoylalanine.

5. The method of claim 1 wherein said N-acyl derivative of an amino acid is N-undecylenoyl-leucine.

6. The method of claim 1 wherein said N-acyl derivative of an amino acid is N-cocoylvaline.

7. The method of claim 1 wherein said compound is applied in an amount of from 10 g/10 ares to 2000 g/10 ares.

* * * * *

UNITED STATES PATENT AND TRADEMARK OFFICE
CERTIFICATE OF CORRECTION

PATENT NO. : 3,947,589
DATED : March 30, 1976
INVENTOR(S) : MISATO, ET AL.

It is certified that error appears in the above-identified patent and that said Letters Patent are hereby corrected as shown below:

Item 75, line 5, delete "; Toshiro Shida"

Item 75, line 6, delete "both of"

Signed and Sealed this fifteenth Day of June 1976

[SEAL]

Attest:

RUTH C. MASON
Attesting Officer

C. MARSHALL DANN
Commissioner of Patents and Trademarks